(12) United States Patent
Patel et al.

(10) Patent No.: US 6,491,870 B2
(45) Date of Patent: *Dec. 10, 2002

(54) OPTICALLY READABLE STRIP FOR ANALYTE DETECTION HAVING ON-STRIP ORIENTATION INDEX

(75) Inventors: Harshad Ishwarbhai Patel, Fremont, CA (US); George Michael Daffern, Sunnyvale, CA (US)

(73) Assignee: LifeScan, Inc., Milpitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/994,316

(22) Filed: Nov. 26, 2001

(65) Prior Publication Data

US 2002/0054827 A1 May 9, 2002

Related U.S. Application Data

(63) Continuation of application No. 08/302,560, filed on Sep. 8, 1994, now Pat. No. 6,335,203.

(51) Int. Cl.[7] .............................................. G01N 21/00
(52) U.S. Cl. ..................... 422/58; 422/68.1; 422/82.05; 436/169
(58) Field of Search .............................. 422/68.1, 82.05, 422/58, 56; 436/169

(56) References Cited

U.S. PATENT DOCUMENTS

| | | |
|---|---|---|
| 3,552,928 A | 1/1971 | Fetter |
| 3,907,503 A | 9/1975 | Betts et al. |
| 3,980,437 A | 9/1976 | Kishimoto et al. |
| 3,992,158 A | 11/1976 | Przybylowicz et al. |
| 4,042,335 A | 8/1977 | Clement |
| 4,125,372 A | 11/1978 | Kawai et al. |
| 4,144,306 A | 3/1979 | Figueras |
| 4,255,384 A | 3/1981 | Kitajima et al. |
| 4,258,001 A | 3/1981 | Pierce et al. |
| 4,292,272 A | 9/1981 | Kitajima et al. |
| 4,452,887 A | 6/1984 | Kitajima et al. |
| 4,509,859 A | 4/1985 | Markart et al. |
| 4,592,893 A | 6/1986 | Poppe et al. |
| 4,682,895 A | 7/1987 | Costello |
| 4,714,874 A | 12/1987 | Morris et al. |
| 4,774,192 A | 9/1988 | Terminiello et al. |

(List continued on next page.)

FOREIGN PATENT DOCUMENTS

| | | |
|---|---|---|
| DE | 40 35 052 A1 | 11/1989 |
| EP | 0 456 098 A2 | 11/1991 |
| EP | 0 574 134 A2 | 12/1993 |
| GB | 938029 | 8/1961 |
| GB | 1037155 | 7/1966 |
| GB | 2 090 659 A | 7/1982 |
| WO | WO 94/18559 | 8/1994 |

OTHER PUBLICATIONS

"Azo Dyes by Oxidative Coupling" S. Hunig and Kobrich, Liebigs, *Ann, Chem.* 617, 216 (1958).

"Mechanism for Preventing Bending of Specimen for Urine" Japanese Patent Appl. 2–233742, Sep. 4, 1990.

"New Contributions to the Optics of Intensely Light–Scattering Materials" Part I, *Journal of Optical Society of America*, vol. 38, No. 5., May 1948, pp. 448–457.

Primary Examiner—Lyle A. Alexander
(74) Attorney, Agent, or Firm—Carol LaSalle, Bozicevic, Field & Francis (57) ABSTRACT

A test strip is provided for determining the presence or quantity of an analyte in a liquid by inserting the strip into an optical reading apparatus. The test strip is provided with an orientation index zone having a reflectance that contrasts with the reflectance of areas contiguous thereto and such orientation index zone is employed to affirm that the test strip has not been inserted upside down with respect to the apparatus.

11 Claims, 6 Drawing Sheets

U.S. PATENT DOCUMENTS

| | | |
|---|---|---|
| 4,790,979 A | 12/1988 | Terminiello et al. |
| 4,816,224 A | 3/1989 | Vogel et al. |
| 4,978,503 A | 12/1990 | Shanks et al. |
| 4,994,238 A | 2/1991 | Daffern et al. |
| 5,029,583 A | 7/1991 | Meserol et al. |
| 5,037,614 A | 8/1991 | Makita et al. |
| 5,059,394 A | 10/1991 | Phillips et al. |
| 5,082,516 A | 1/1992 | Akao et al. |
| 5,095,025 A | 3/1992 | Tanaka et al. |
| 5,095,026 A | 3/1992 | Schoenwald et al. |
| 5,120,507 A | 6/1992 | Sano et al. |
| 5,167,145 A | 12/1992 | Butler et al. |
| 5,174,963 A | 12/1992 | Fuller et al. |
| 5,192,502 A | 3/1993 | Attridge et al. |
| 5,211,914 A | 5/1993 | Vogel et al. |
| 5,232,668 A | 8/1993 | Grant et al. |
| 5,236,940 A | 8/1993 | Audiau et al. |
| 5,246,858 A | 9/1993 | Arbuckle et al. |
| 5,252,293 A | 10/1993 | Drbal et al. |
| 5,277,870 A | 1/1994 | Fuller et al. |
| 5,304,468 A | 4/1994 | Phillips et al. |
| 5,306,623 A | 4/1994 | Kiser et al. |
| 6,335,203 B1 * | 1/2002 | Patel et al. .................. 436/169 |

* cited by examiner

OPTICALLY READABLE STRIP FOR ANALYTE DETECTION HAVING ON-STRIP ORIENTATION INDEX

CROSS-REFERENCE TO RELATED APPLICATION

This application is a continuation of U.S. application Ser. No. 08/302,560, filed Sep. 8, 1994, now issued as U.S. Pat. No. 6,335,203.

FIELD OF THE INVENTION

The present invention relates to a test device and method for the optical determination of analytes in aqueous fluids, particularly whole blood. In one preferred embodiment it concerns a test device and method for optically measuring the concentration of glucose in whole blood.

BACKGROUND OF THE INVENTION

The quantification of chemical and biochemical components in colored aqueous fluids, in particular colored biological fluids such as whole blood and urine and biological fluid derivatives such as blood serum and blood plasma, is of ever-increasing importance. Important applications exist in medical diagnosis and treatment and in the quantification of exposure to therapeutic drugs, intoxicants, hazardous chemicals and the like. In some instances, the amounts of materials being determined are either so minuscule—in the range of a microgram or less per deciliter—or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Currently a method widely used in the United States employs a test article of the type described in U.S. Pat. No. 3,298,789 issued Jan. 17, 1967 to Mast. In this method a sample of fresh, whole blood (typically 20–40 $\mu l$) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another popular blood glucose test method employs similar chemistry but uses, in place of the ethylcellulose-coated pad, a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then, in the first case, the blood sample is washed off with a stream of water while in the second case, it is wiped off the film. The reagent pad or film is then blotted dry and evaluated. The evaluation of the analyte concentration is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator calorimetric determinations in that their result is based on an absolute color reading which is in turn related to the absolute extent of reaction between the sample and the test reagents. The fact that the sample must be washed, blotted or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing, overblotting or overwiping can give low results and underwashing can give high results.

Another problem that often exists in simple lay-operator determinations is the necessity for initiating a timing sequence when blood is applied to a reagent pad. A user will typically have pricked his or her finger to obtain a blood sample and will then be required to simultaneously apply the blood from the finger to a reagent pad while starting a timer with his or her other hand, thereby requiring the use of both hands simultaneously. This is particularly difficult since it is often necessary to ensure that the timer is started only when blood is applied to the reagent pad. All of the prior art methods require additional manipulations or additional circuitry to achieve this result. Accordingly, simplification of this aspect of reflectance reading instruments is desirable.

Great improvements have been achieved upon the introduction of the systems described in U.S. Pat. Nos. 5,179,005, 5,059,394, 5,049,487, and 4,935,346 wherein an apparatus is provided for accepting a test strip having a test pad, one surface of which comprises a reaction zone adapted to be optically readable by said apparatus. The test strip is inserted into the apparatus, the apparatus is started and then whole blood is applied onto the test pad. At least a portion of such blood is allowed to permeate to the reaction zone whereby any analyte present therein will react with color-producing reagents in the test pad to alter the light reflectivity characteristics of the reaction zone. The reflectivity of the reaction zone is then a measure of the presence and/or quantity of analyte present in the blood sample. As described in the aforementioned patents, this system does not require a large sample of blood nor does it require the user to undertake timed manipulations with respect to the beginning or end of the reaction. Instead, because the strip is first inserted into the apparatus prior to the application of the sample, a standard reflectance reading of the reaction zone in the dry state may be obtained. The beginning of the reaction can be detected by the first "breakthrough" of the liquid sample onto the reaction zone by monitoring the reflectance and comparing the reading to the standard reflectance of the dry reaction zone. A reflectance reading taken at a predetermined time after the reaction has begun and compared to the standard reflectance, i.e., the dry reaction zone reading, will be indicative of the quantity of analyte present in the sample.

While the above described system does indeed solve the problems of the prior art and relieves the user of the burden of measurement and timing, it does require that the user apply a sample of blood onto the strip while the strip is in the apparatus. For the most part this represents no problem to the vast majority of users. However, certain users suffer from handicaps such as poor vision or impaired motor coordination so that the accurate application of blood from such users' pricked fingers to the strip, in place on the apparatus, represents a hardship. Further, for institutional users, for example, there is the possibility that some quantity of blood remains on the device from a prior user, since the systems necessitate applying one's pricked finger to the device. In such instances there is the need to disinfect the device between users.

Accordingly, for the above reasons, in the case of at least some users, it would be preferable to first apply the blood sample to the strip prior to inserting the strip into the apparatus. Unfortunately, by doing so the apparatus no longer has the capability of reading reflectance of the dry, unreacted, reaction zone, i.e., at no time is the dry reaction zone presented to the apparatus. This reading was necessary in the prior devices to provide a calibration standard for determining the reflectance change as a result of the reaction and hence the presence and/or quantity of the analyte in the sample.

In a commonly assigned, copending U.S. patent application Ser. No. PCT/US95/12156 filed today entitled "Optically Readable Strip For Analyte Detection Having On-Strip Standard", and incorporated herein by reference, there is described a strip, apparatus, and methodology for allowing the user to apply a sample to the strip before inserting it into the reading apparatus while also providing a calibrated standard. This above-referenced patent application teaches a strip which comprises a portion for having the liquid applied thereto, this portion having an optically visible surface (i.e., at least with respect to the optics of the apparatus to be employed with the strip) defining a reaction zone. The reaction zone is such that its reflectance varies as a function of the quantity of analyte present in the applied liquid. Preferably, such is accomplished by the analyte, if present, reacting with reactants to produce a color change of the reaction zone. The test strip further comprises an optically visible standard zone of high reflectance, relative to the reflectance of the reaction zone. The standard zone is positioned on the strip so as to lead the reaction zone as the strip is inserted into the apparatus.

Accordingly, the apparatus may be provided with optical means for sequentially determining the reflectance value of the standard zone as the strip is being inserted into its fully inserted position in the apparatus and the reflectance value of the reaction zone after the strip has been inserted. Additionally, the apparatus is provided with means for calculating the presence and/or quantity of the analyte in question as a function of the standard zone reflectance and the reaction zone reflectance.

Owing to the configuration of the strip as described and specifically, the provision of a standard zone leading the reaction zone, the aforementioned apparatus need be provided with only one set of optics, e.g., one light emitting diode and one light detector for reading the reflection at a single position along the path of the strip.

In operation, the user turns on the apparatus, applies the sample to a fresh strip and then inserts the strip fully into the apparatus and reads the results. Without intervention of the user, the strip, configured as described, allows the apparatus to read the reflectance of light incident upon the standard zone as it passes the optics of the apparatus as the strip is inserted. This reading is then calibrated to account for variations owing to changes in the apparatus from the factory condition and to lot-to-lot variations in the strip. The fully inserted strip thereafter presents the reaction zone to the optics of the apparatus and the reflectance of this surface may be read. Means are provided for the apparatus to calculate and report the analyte presence or concentration as a function of these readings.

The above-described system has gone a long way toward easing the user's task in determining analyte concentration. It will be appreciated, however, that it is fundamental to the successful optical reading of a strip on which liquid has been applied, that the strip be properly oriented when inserted into the apparatus.

Specifically, in a surprising number of cases, the strip is improperly introduced upside down with a resultant erroneous reading. At best, such an error, if not caught immediately, requires discarding the strip, which can be contaminated or otherwise altered in the erroneous attempt to use it upside down and repeating the process with a fresh strip. Obviously, in the case of a blood sample requiring another finger pricking, this is highly undesirable. In the worst case, the erroneous results may be accepted by the user with potentially adverse consequences.

A prior art device sold by the Boehringer-Mannheim Company under the trademark Accutrend® is provided with a black band on the trailing end of the strip. The apparatus for use with such a strip appears to be provided with two sets of optics; one to read a first zone and the second to read the black band. It appears that the apparatus is provided with microprocessing means for recording the absence of detection of such black band by the second set of optics. Such absence would be indicative of the strip having been inserted upside down. Unfortunately, the system adds great complexity and costs to design and manufacture of the apparatus in that two sets of optics are required. Moreover, any detection of an improperly inserted strip occurs only after the entire operation; i.e., insertion of the strip, has been completed; that is to say, at the last possible moment.

Accordingly, there is a need to provide a system wherein the upside down insertion of a strip is immediately detected and to accomplish this without the need for expensive modification of the strip reading apparatus.

SUMMARY OF THE INVENTION

In accordance with the teachings of this invention, a strip, method and apparatus are provided for determining the presence or quantity of analyte or liquid by inserting the strip into an optical reading apparatus wherein means are provided for rapidly and simply affirming that the strip has not been inserted upside down with respect to the optics of the apparatus.

Specifically, the strip comprises a portion for having a liquid (e.g. blood) applied thereto. This portion has an optically visible area on a major surface of the strip defining a reaction zone which varies in reflectance as a function of the quantity of analyte present in the applied liquid. The test strip is further provided with an optically visible area on the same major surface which defines an orientation index zone and is positioned within that portion of such major surface leading the reaction zone as the strip is inserted into the apparatus. The orientation index zone is selected to have a contrasting reflectance relative to the areas of the major surface contiguous with this orientation index zone. Accordingly, the apparatus, utilizing the same optics provided to read the reflectance of the reaction zone once the strip is fully inserted, may also employ such optics to sequentially determine the reflectance value of the portion of the major leading surface of the strip as the strip is being inserted into the apparatus. Such optics will experience a sharp change in reflectance as the interface between the orientation index zone and the areas of the major surface contiguous therewith pass over the optics; such change being indicative of a properly inserted strip. Microprocessing means may be provided in the apparatus for processing the reflectance experienced by the optic system and for either detecting the presence of the orientation index or for reporting its absence.

In view of the above teachings, it can be seen that merely by positioning an orientation index zone on the leading portion of the surface to be read, the detection of an upside down strip can be made at the earliest possible moment as the strip is being inserted with no need for additional optical equipment.

BRIEF DESCRIPTION OF THE DRAWINGS

The present invention can be more readily understood by reference to the following detailed description when read in conjunction with the attached drawings wherein.

DETAILED DESCRIPTION OF THE INVENTION

Figure 1:
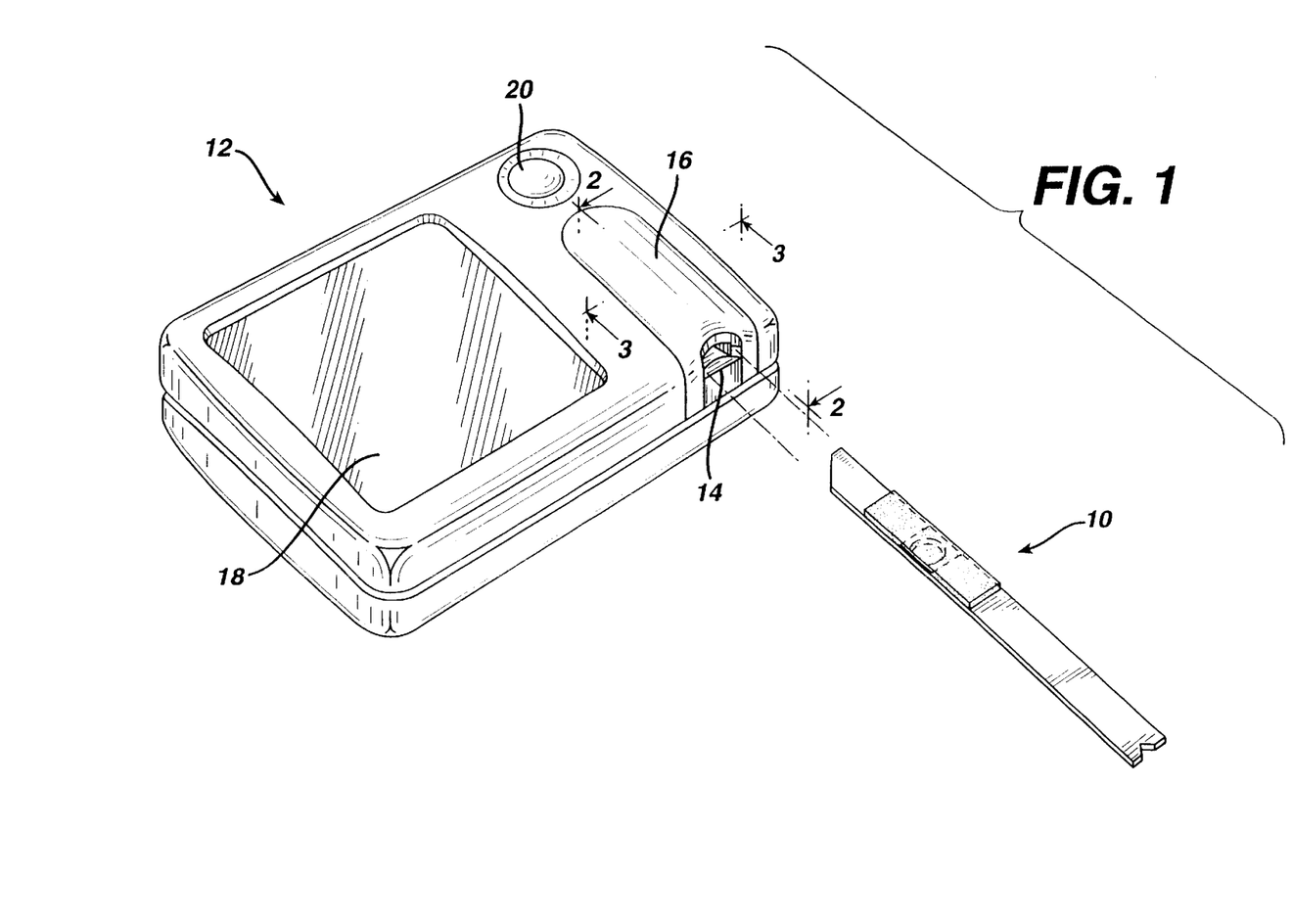
FIG. 1 is an exploded, perspective view of a strip and apparatus embodying the teachings of this invention.

Turning now to the drawings, FIG. 1 illustrates an exploded, perspective view, a strip 10 for applying a sample thereon and for inserting such sample laden strip 10 into an optical reading apparatus 12. The embodiments of the strip 10 and apparatus 12 will generally be described hereinafter in terms of detection and quantification of glucose but it will be understood by those skilled in the art that the teachings herein are not limited to glucose determinations, and instead may be applied to other analyte determinations. Further, for the purposes of simplification and clarity, the strip 10, the apparatus 12 and their respective component parts shall all be described as being in the orientation shown in the drawings and terms such as "the bottom" and "the top" shall be employed consistent with such orientation. It will be appreciated, however, that this method of description is merely convenient and that in no way is the invention restricted to such orientation and, in fact, the strip and strip holder may be rotated through any angle relative to the apparatus and the teachings herein shall still apply.

Figure 2:
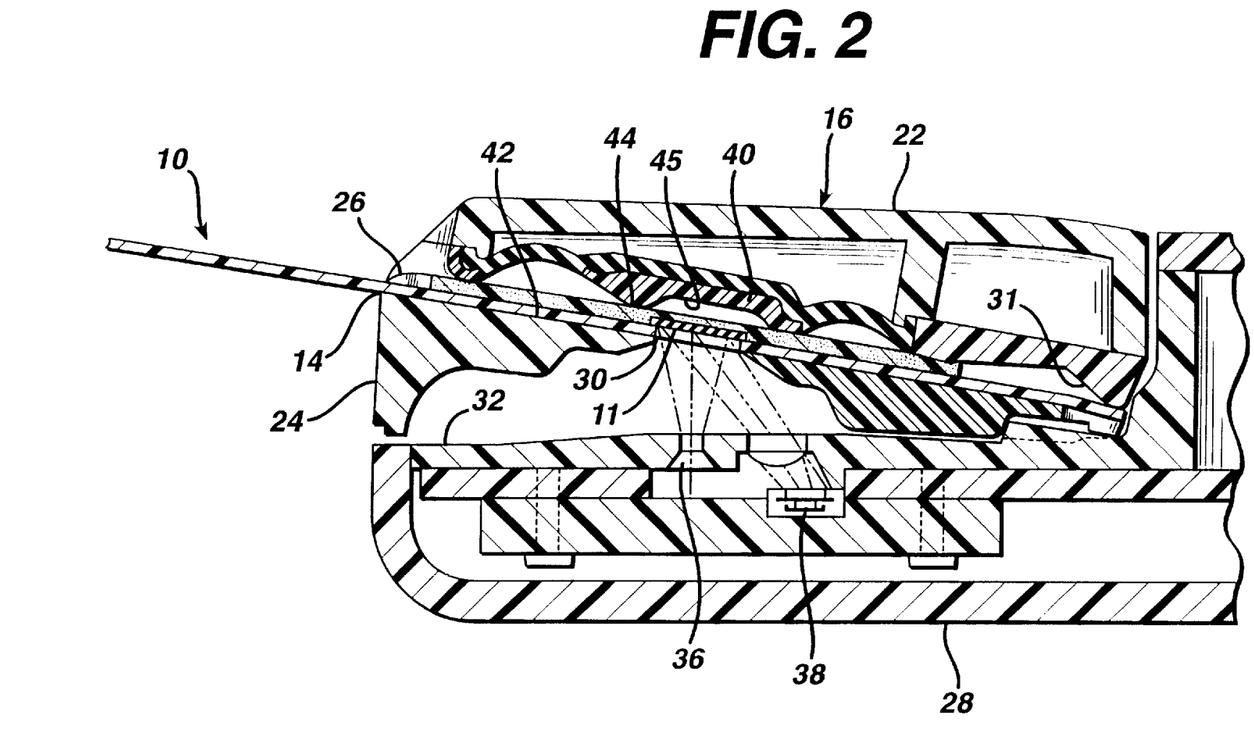
FIG. 2 is a partial, longitudinal, cross-sectional view taken along line 2—2 of FIG. 1 and illustrating the strip fully inserted into the apparatus.
Figure 3:
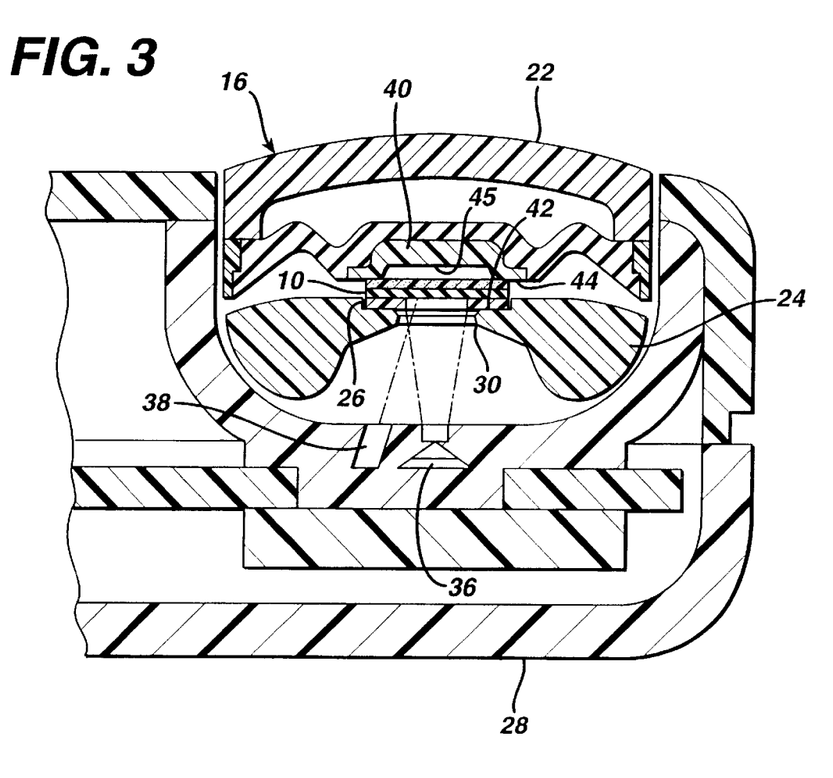
FIG. 3 is a partial, transverse, cross-sectional view, taken along line 3—3 of FIG. 1 and illustrating the strip fully inserted into the apparatus.

As can be seen in FIG. 1, the strip 10 is adapted to be inserted longitudinally, into an opening 14 of a strip holder 16 carried on apparatus 12. Strip holder 16, shown in more detail in FIGS. 2 and 3, is preferably removable from apparatus 12 for cleaning. The apparatus 12 is provided on its visible surface with a screen 18 on which messages, instructions, error warnings, and most importantly, results may be displayed by means such as liquid crystal displays as are well known in the art. Such information may be conveyed by letters, words, numbers or icons. Additionally, apparatus 12 is provided with a power switch for activating the apparatus, preferably with batteries and such power switch is shown as push button 20 on the drawings.

Referring now to FIGS. 2 and 3, illustrated therein in longitudinal and transverse cross-sectional views respectively, is the removable strip holder 16 with a strip 10 fully inserted therein, together with fragmentary views of the adjacent parts of the apparatus 12. The strip holder 16 is comprised of an upper guide 22 and a lower guide 24 which together form a channel or strip passageway 26 into which the strip is inserted via opening 14. The extent of insertion of the strip is determined by strip impeding wall 31. It should be noted that the passageway 26 is canted at an angle with respect to the plane of the bottom 28 of the apparatus 12, so as to facilitate the insertion of strip 10 into the apparatus when the apparatus is sitting on a flat surface.

The lower guide 24 is provided with an aperture 30 through which the bottom surface 11 of the strip 10 can be "seen" by the optics located below lower guide 24. As will be understood hereinafter, the aperture 30 is positioned along the lower guide 24 so as to "see" the bottom surface of a reaction zone of strip 10 when the strip 10 is fully inserted into passageway 26.

The optics for the apparatus are located in optic block 32 affixed to apparatus 12. Optic block 32 contains a light emitting diode (LED) 36 capable of directing light through aperture 30, upon a surface such as the lower surface 11 of the strip. The light emitting diode is preferably one which emits light of essentially a uniform wavelength in rapid bursts, hereinafter referred to as "chops", for a period of time, each time it is activated. For the purposes of glucose determination it has been found preferable to employ two such LED's, each emitting light at a different wavelength and preferably at 660 and 940 nanometers (LED 660 and LED 940, respectively). The optic block 32 also comprises a photodetector 38, a device capable of intercepting light reflected from the surface upon which the LED's focus and converting such light into a measurable voltage.

Incorporated into the upper guide 22 is bias means 40 which is adapted to be biased toward the upper surface 42 of the lower guide in the area of the aperture 30 so as to ensure that the portion of the strip 10 lying over the aperture 30 is flat and presents an optically consistent surface to the optics. As illustrated in the drawings, bias means 40 comprises an elastomeric membrane having, on its surface opposing the aperture, a ring-like projecting gasket 44 which is adapted to bear against the strip when in place and hold the strip flat to the aperture. Centered within the ring-like projection is a colored target, preferably gray, hereinafter referred to as the "gray target" 45. The gray target 45 presents to the optics a surface for assuring the correct calibration of the apparatus before the strip is inserted. Additionally, it is the gray target that is "seen" by the optics once the apparatus is turned on and before a strip is inserted.

The bias means 40 may take forms other than that of an elastomeric membrane. For example, a leaf spring can be used as such bias means. In a copending, commonly assigned U.S. patent application Ser. No. PCT/US95/12089 filed today (incorporated herein by reference), such alternative bias means are described and include a particularly useful means in which the passageway 26 is designed in a serpentine configuration which in combination with a strip having spring properties serves to function as a bias means. Such a passageway is illustrated in FIG. 7 wherein upper guide 22 and lower guide 24 are illustrated.

Table 1, below, recites preferred dimensions for the angles, distances and radii; all based on the X,Y coordinates shown in the Figure.

TABLE 1

Figure 7:
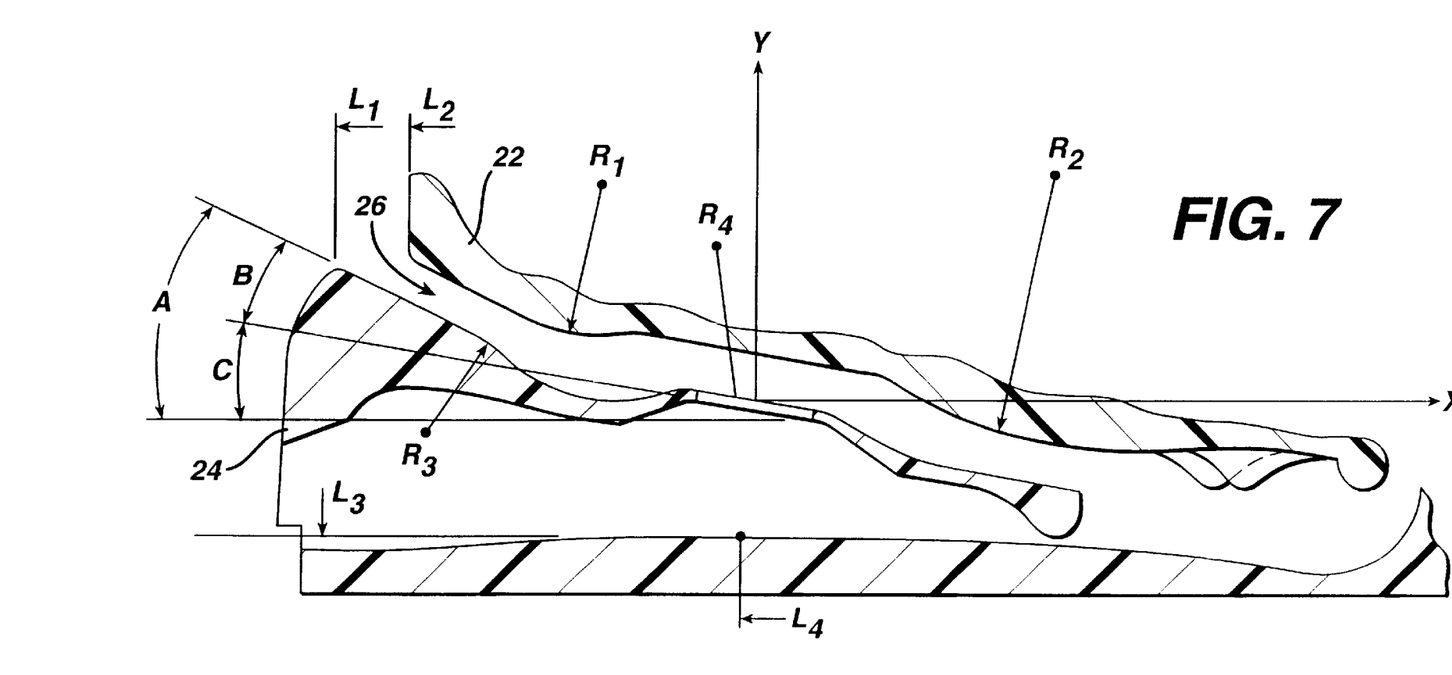
FIG. 7 is a cross-sectional view of a strip passageway of an embodiment of an apparatus employing the teachings of this invention.

DIMENSIONS FOR FIG. 7

| ANGLES (Degrees) | |
|---|---|
| A | 26 |
| B | 17 |
| C | 9 |

| DISTANCES (Inches) | |
|---|---|
| $L_1$ | 0.562 |
| $L_2$ | 0.467 |
| $L_3$ | 0.184 |
| $L_4$ | 0.013 |

| CURVATURE | | |
|---|---|---|
| | RADIUS (Inches) | CENTER (X, Y In) |
| $R_1$ | 0.2 | 0.207, 0.179 |
| $R_2$ | 0.347 | 0.391, 0.300 |
| $R_3$ | 0.100 | 0.417, 0.006 |
| $R_4$ | 2.635 | 0.412, 2.603 |

Figure 4:
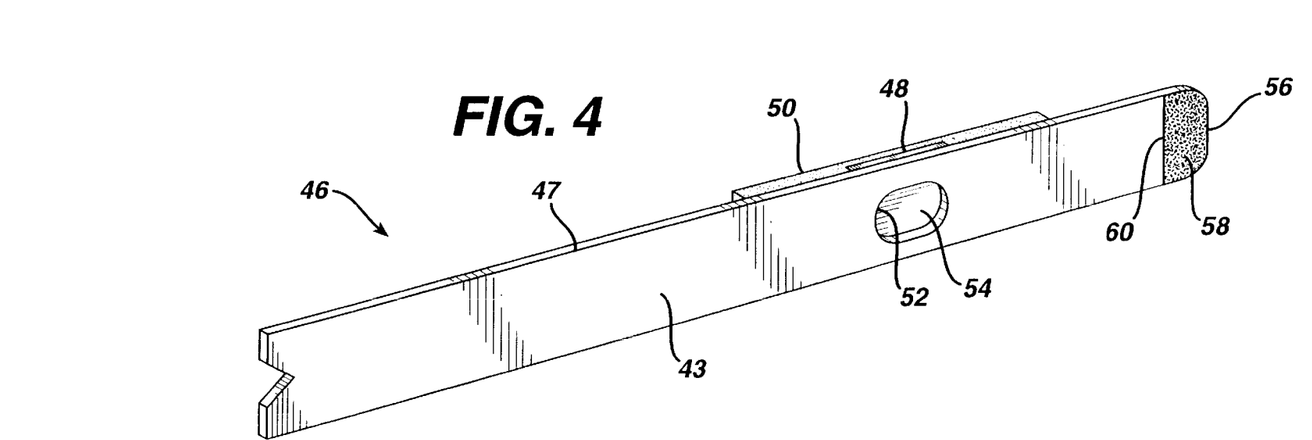
FIG. 4 is a perspective view illustrating the leading portion of the major surface of a first embodiment of the strip of this invention.

Referring now to FIG. 4 illustrated therein is a perspective view of the bottom major surface 43 of a strip 46 embodying the teachings of this invention.

In the embodiment described herein for detecting glucose in whole blood, the strip 46 comprises an elongate and generally rectangular support 47 onto which is attached a test pad 48 containing reactants and provided with an overlying transport medium 50. In use the sample is to be applied to the top surface of the transport medium 50 overlying the test pad 48. A portion of the sample penetrates through the test pad and any glucose present reacts with the reactants therein to produce a color change which is visible on the bottom surface of the test pad. A support aperture 52 is provided through the support for aligning with aperture 30 in the lower guide of the apparatus when the strip is fully inserted therein, so that a portion of the bottom of the surface of the test pad will be visible to the optics of the apparatus (such portion hereinafter, the reaction zone).

Details of these components of the strip are described in copending U.S. Ser. No. 881,970, filed on May 12, 1992 and incorporated herein by reference. Briefly, the transport medium 50 comprises pores which draw the sample therethrough by capillary action. The transport medium may be composed of natural materials such as cotton or paper, as well as such synthetic materials as polyesters, polyamides, polyethylene and the like.

The transport medium has pores having an effective diameter in the range of about 20 microns to about 350 microns, preferably about 50 to about 150 microns, e.g., 100 microns. The transport medium is generally hydrophilic or may be rendered hydrophilic by treatment with surfactants compatible with red blood cells. One such compatible surfactant is MAPHOS™ 66 sold by Mazer Chemical, a division of PPG Industries Inc. Chemicals of Gurnee, Ill. In a preferred embodiment, the transport medium is capable of absorbing blood samples of up to about 20 to about 40 microliters e.g., 30 microliters.

The transport medium may be, for example, a filter paper or sintered plastic material, such as those porous polyethylene materials commonly available from the Porex Corp. of Fairburn, Ga. The transport medium is generally fabricated to have a thickness of about 0.022 inch, with about 0.25 inch width and about 1.0 inch length. The transport medium is treated with a red blood cell compatible surfactant solution. Since only about 3 to about 5 microliters of blood are required to saturate the testing pad, the transport medium will preferably possess a small void volume in order not to require large volumes of blood. Excess blood applied to the reagent strip is absorbed and held in the portion of the transport medium which extends beyond the test pad.

The test pad and its preparation are also set forth in detail in U.S. Pat. No. 4,935,346 and need not be described in detail herein. Essentially, the test pad is a hydrophilic porous matrix to which reagents may be covalently or non-covalently bound. Examples of a suitable material include polyamides, which are conveniently condensation polymers of monomers of from 4 to 8 carbon atoms, where the monomers are lactams or combinations of diamines and dicarboxylic acids, polysulfones, polyesters, polyethylene, and cellulose based membranes. Other polymeric compositions may also be used. Further, the polymer compositions may be modified to introduce other functional groups so as to provide for charged structures, so that the surfaces may be neutral, positive, or negative, as well as neutral, basic, or acidic. The material of choice is a hydrophilic, anisotropic polysulfone membrane having pores varying in size from large to small through the thickness of the matrix. The preferred matrix is obtained from the Memtec America Corporation of Maryland and has an average pore size ranging from 0.34 to 0.4 micrometers e.g., 0.37 and a thickness of from about 125 to about 140 micrometers e.g., 130 micrometers. The ratio of the average diameter of the large to the small pores is about 100.

Transport medium 50 is attached to the test pad 48 by an adhesive (not shown). Suitable adhesives for this purpose, including acrylic, rubber, and ethylene vinyl acetate (EVA) based formulations. Particularly useful are the hot melt adhesives known in the art. The adhesive may be placed in continuous stripes located only near the perimeter of the test pad, leaving a central portion of the receiving surface of the test pad substantially unobstructed.

Alternatively, when the transport layer is composed of a material that fuses at industrially practical temperatures, the transport layer may be attached directly to the test pad by an application of heat and pressure. The transport layer is heated until it begins to melt and then pressed against the testing pad and cooled. Direct attachment of the transport layer to the testing pad by fusion obviates any need for a distinct adhesive layer.

The adhesive layer connects the transport medium to the sample receiving surface of the test pad. The transport medium is adapted to accept a whole blood sample and transport a detectable portion of the sample to the receiving surface by capillary action. The transport medium preferably extends past one or more ends of the test pad so as to form a reservoir for holding excess amounts of blood sample which may be present during actual use. It is usually more desirable to retain such excess amounts of the blood sample in the transport medium, rather than allowing the excess to drip upon the user or upon the viewing means in an uncontrolled fashion. Accordingly, it is preferred that the transport medium be capable of holding from about 20 to about 40 microliters of blood, preferably about 30 microliters of blood and of passing from about 3 to about 5 microliters of blood to the test pad.

The test pad is impregnated with a color forming reagent system specific to an analyte. Typical analytes are glucose, cholesterol, urea, and many others which will readily occur to those skilled in the art. Preferably, the color forming reagent system includes an enzyme which selectively catalyzes a primary reaction with the analyte of interest. A product of the primary reaction may be a dye which undergoes a change in color that is detectable at the reaction zone. Alternatively, the product of the primary reaction may be an intermediate which undergoes another reaction, preferably also enzyme catalyzed, and participates in a secondary reaction which, directly or indirectly, causes a dye to undergo a change in color which is detectable at the reaction zone.

An exemplary color-forming reagent system is the system which is specific to glucose and contains glucose oxidase, a peroxidase, and an oxidizable dye. Glucose oxidase is an enzyme, usually obtained from Aspergillus Niger or Penicillium, that reacts with glucose and oxygen to produce gluconolactone and hydrogen peroxide. The hydrogen peroxide so produced, catalyzed by a peroxidase enzyme such as horseradish peroxidase, oxidizes a dye. The resulting chromophore (the oxidized dye) exhibits a color that may be observed at the reaction zone. Many suitable oxidizable dyes are known in the art including, for example, those set out in U.S. Pat. No. 5,304,468, incorporated herein by reference. One particularly useful oxidizable dye is the 3-methyl-2 benzothiazolinone hydrazone hydrochloride/8-amilino 1-naphthalenesulfonate dye couple (MBTH/ANS couple) described in copending U.S. patent application Ser. No. 245,940, filed May 19, 1994. Many other suitable color-forming reagent systems specific to particular analytes are known in the art. A dye couple of choice is a derivative of MBTH, meta [3-methyl 2-benzothiazolinone hydrazone] N-sulfonyl benzenesulfonate monosodium coupled with ANS. This combination is described in detail in U.S. patent application Ser. No. PCT/US95/12091 filed today and incorporated herein by reference.

The support 46 may be of a material that is sufficiently rigid to be inserted into the apparatus without undue bending or kinking. Preferably, such support comprises materials such as polyolefins (e.g., polyethylene or polypropylene), polystyrene or polyesters. A preferred material is the polyester available from the Imperial Chemical Industries, Ltd. of the United Kingdom, sold by them under the trademark Melinex 329 and having a thickness of about 0.014 inches.

Referring to FIG. 4, the bottom surface of the strip (i.e., the surface to be inserted in face-to-face relationship with the aperture 30 of the lower guide of the apparatus and hence the surface "seen" by the optics of the apparatus), presents a reaction zone 54 comprising the portion of the test pad 48 visible through the support aperture 52. The reaction zone 54 is longitudinally placed between the leading edge 56 of the strip (leading with respect to insertion into the apparatus) and the opposite edge. In accordance with the teachings of this invention, the portion of the major surface 43 leading the reaction zone 54 includes an optically visible area; (i.e., visible to the optics of the apparatus 12 as the strip is inserted therein) defining an orientation index zone 58. As illustrated in FIG. 4, preferably this orientation index zone 58 is located at the extreme leading edge of the leading portion of the major surface 43. The orientation index zone 58 is characterized as having a low reflectance relative to that of the area of the major surface 43 contiguous to the orientation index zone 58. Thus, when interface 60, between the orientation index zone 58 and the area contiguous thereto, passes over the optics of the apparatus as a strip is inserted, the optics will detect a sharp rise in reflected light.

Figure 5:
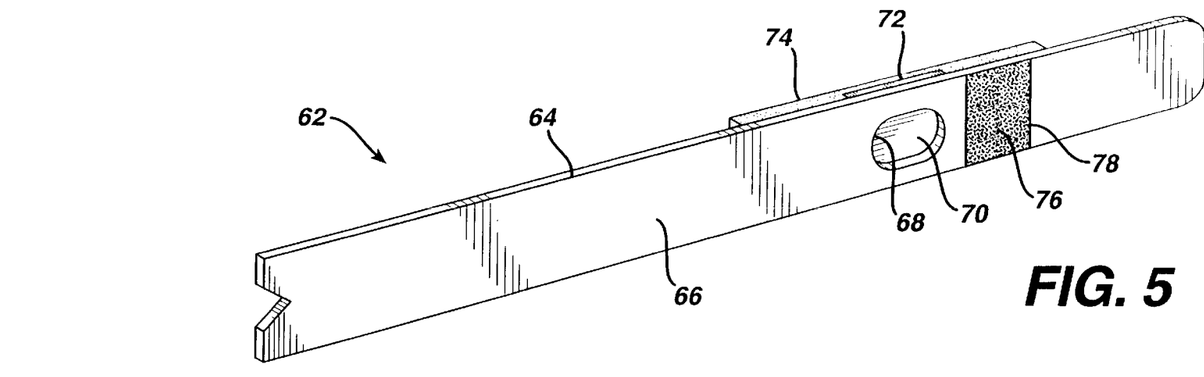
FIG. 5 is a perspective view illustrating a major surface of a second embodiment of the strip of this invention.

FIG. 5 illustrates an alternative embodiment 62 of the strip. As in the prior described embodiment, the strip 62 comprises a support 64 having a major surface 66 with an aperture 68 therethrough for viewing a reaction zone 70 of a test pad 72. The test pad is again provided with a transfer medium 74. In this embodiment, an orientation index zone 76 is placed on the leading portion of a major surface 66 but in this instance adjacent to the aperture 70. Again, the orientation index zone 76 is characterized as having a low reflectance relative to that of the areas of the major surface 66 contiguous thereto. Thus, for this embodiment, when interface 78 between the orientation index zone 76 and the area contiguous thereto passes over the optics of the apparatus as the strip is inserted therein, the optics will detect a sharp decrease in reflected light.

The desired low relative reflectance of the orientation index zone may be achieved on a major surface of a strip of this invention by any number of ways as will occur to one skilled in the art. For example, the support may have laminated to it, in a desired region, a layer having the requisite reflectance. Alternatively, the material comprising the support may have incorporated therein a coloring material imparting the proper reflectance to the region comprising the orientation index zone. As further alternatives, the coloring material may be printed or painted onto the appropriate region.

While the method chosen for accomplishing the contrasting reflectance values between the orientation index zone and the contiguous area of the major surface is not critical, it is important that a minimal change in reflectance is exhibited across the interface between these areas. Accordingly, for the embodiment shown in FIG. 4, the reflectance of the contiguous portion of the major surface should be at least 1.5 times that of the reflectance of orientation index zone 58. Preferably, the reflectance should be at least two times as high. Similarly, for the embodiment shown in FIG. 5, the reflectance of the orientation zone should be no more than two thirds of the reflectance of the contiguous portion of the major surface. Preferably, the reflectance should be only half that of the contiguous portion.

In a preferred embodiment, the microprocessor of the apparatus may be programmed to sense the difference between the reflectance of an empty passageway, i.e., the reflectance of the gray target in the embodiment illustrated herein, and that of the orientation index zone. In such case, the reflectance of the orientation zone, should be less than 0.9 times the reflectance of the gray target. Preferably this value is less than 0.5 times.

It will be understood that these relative reflectance values are those detected by the specific apparatus using light having a wavelength of 940 nanometers.

Further, it will be understood that the length of the orientation index zone must be sufficient in the direction of insertion so as to provide the optics with adequate time to produce a number of readings and, hence, experience the change in reflectance across the interface. It has been found that a length in the direction of insertion of from about 0.05 to about 0.4 inches is adequate and preferably such length should be from about 0.15 to about 0.25 inches.

In accordance with the teachings of our copending U.S. patent application Ser. No. PCT/US95/12156, referred to above and incorporated herein by reference, the area of the major surface leading the reaction zone comprises a standard zone exhibiting high reflectance. As is well described in the referenced patent application, the reflectance of this standard zone is calibrated and used together with reflectance of the reaction zone to calculate the quantity of analyte present in a sample. In the embodiments illustrated in FIGS. 4 and 5, the portions of the major surface leading the reaction zone (other than the orientation index zone) are provided to have such high relative reflectance and, hence, may serve as the standard zone in accordance with the teachings of the above-referenced patent application. It will be understood, however, that the teachings of this invention are not limited to being used together with the standard zone described above, but instead may be employed in other test strips.

As described in conjunction with the drawings, the strip is "read" by the apparatus as it is being inserted into the apparatus and the various areas of the leading major surface pass over the aperture 30 of the apparatus making such areas visible to the optics. In its final position, the reaction zone overlies the aperture 30 and is read. Reading is accomplished by directing light from a light emitting diode onto the visible surface and detecting the light reflected from such surface. When employing the teachings of this invention to detect glucose in blood, for example, LEDS emitting light at wavelengths of 660 and 940 nanometers are preferred.

As stated, the reflectance of the surface presented to the optics is measured in multiple readings as the strip is inserted into the apparatus. These multiple readings are taken as the strip moves continuously through various positions in spaced periods of time. Each such reading comprises a number of bursts of energy imparted to the LED in response to directions from a microprocessor. These bursts, referred to as chops, control the amount of light energy directed to the surface for each reading, i.e., at a constant power level, the greater the number of chops the greater amount of light energy incident upon the surface being measured. The light energy reflected by the surface during each reading is captured by a photodetector and converted into a measurable signal by a dual slope analog to digital converter.

Figure 6:
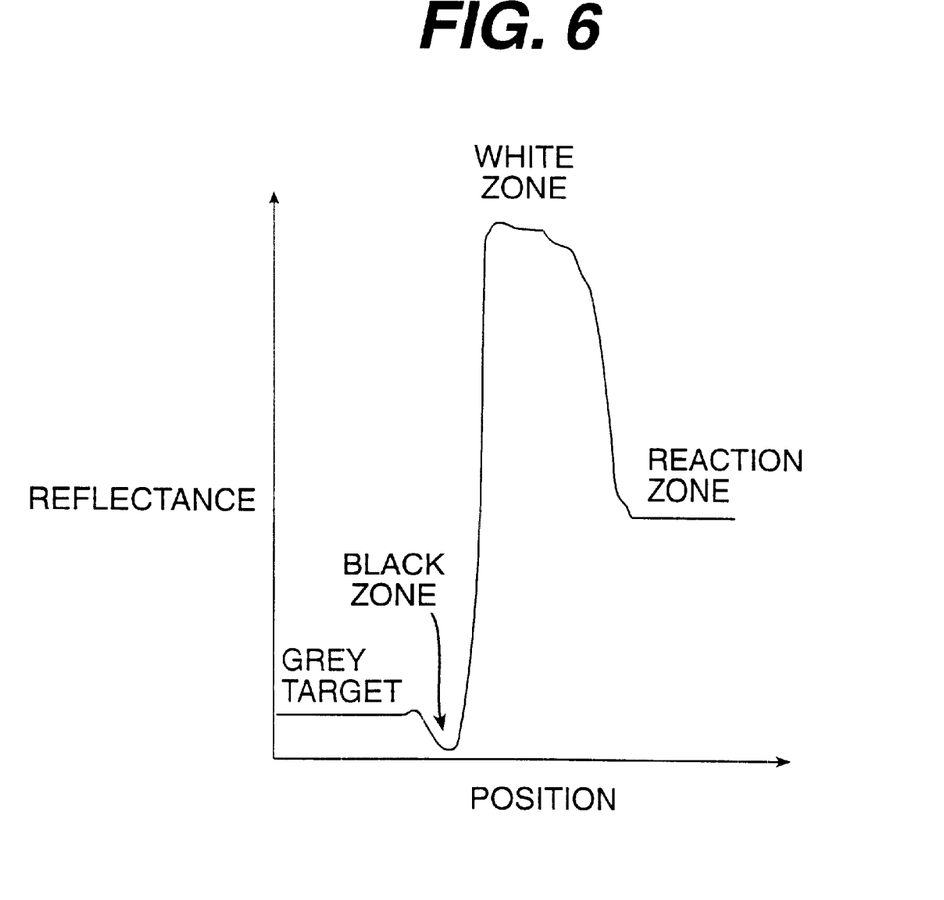
FIG. 6 is a graphical depiction of the detection of reflected light as the strip of FIG. 4 is inserted into an optical reading apparatus.

FIG. 6 is a plot of the counts or quantity of detected light reflected from the surface presented to the aperture as a function of time as the apparatus is turned on and then the strip of FIG. 4 is inserted therein. As can be seen, when the apparatus is first turned on, the measured reflectance is that of the gray target which is chosen to be of moderately low reflectance value. Immediately upon the strip being inserted, the reflectance measured is that of the orientation index zone; e.g., zone 58 in FIG. 4. As seen in FIG. 6, this results in a sharp detected drop in reflectance. The microprocessor of the apparatus may be programmed to accept a strip causing such a sharp initial drop as a properly inserted strip and, hence, continue with the operation of the instrument or, failing to detect such a drop, report that the strip has been inserted improperly. Alternatively, the reading of the reflectance may continue as the orientation zone passes over the aperture. Upon the orientation index zone passing beyond the aperture, the contiguous zone of the leading major surface become visible to the optics, and a sharp increase in the reflectance is exhibited. At this point, the microprocessor may be programmed to accept the strip causing such a sharp increase as a properly inserted strip and to continue with the operation of the instrument. Again, failing to detect such increase, the microprocessor can report that the strip has been inserted improperly.

Assuming detection of the proper orientation of the strip, the reflectance of the white zone and the reflectance of the reaction zone are read and the analyte concentration is determined as a function of these values.

The invention now being fully described, it will be apparent to one of ordinary skill in the art that modifications and changes may be made thereto without departing from the spirit and scope of the present invention.

What is claimed is:

1. A test strip for determining the presence or quantity of an analyte in a liquid by inserting said test strip into an optical reading apparatus; said test strip comprising:
   a portion, for having liquid applied thereto, said portion having an area on a major surface of the strip defining a reaction zone, such reaction zone varying in reflectance as a function of the quantity of analyte in the applied liquid;
   said test strip further comprising an area on said major surface defining an orientation index zone, said orientation index zone being positioned to lead said reaction zone as said strip is inserted into said apparatus;
   said orientation index zone having a contrasting reflectance relative to that of the areas of the major surface contiguous to the orientation index zone;
   whereby said apparatus may be provided with optical means for sequentially determining reflectance values of the major surface as the strip is inserted into the apparatus and with microprocessing means for detecting the presence of the orientation index zone or for reporting its absence.

2. The strip of claim 1 wherein said orientation index zone is positioned on said major surface to lead said contiguous area as the strip is to be inserted into said apparatus.

3. The strip of claim 2 wherein the reflectance of said contiguous area is at least 1.5 times the reflectance of said orientation index zone.

4. The strip of claim 3 wherein the reflectance of said contiguous area is at least two times the reflectance of said orientation index zone.

5. The strip of claim 2 wherein the reflectance of said contiguous area is no more than about 0.67 times the reflectance of said orientation index zone.

6. The strip of claim 5 wherein the reflectance of said contiguous area is no more than about 0.5 times the reflectance of said orientation index zone.

7. The strip of claim 1 wherein the orientation index zone reflects no more than 0.9 times the light reflected when no strip is present in the apparatus.

8. The strip of claim 7 wherein the orientation index zone reflects no more than 0.5 times the light reflected when no strip is present in the apparatus.

9. The strip of claim 1 wherein the orientation index zone reflects at least 1.1 times the light reflected when no strip is present in the apparatus.

10. The strip of claim 9 wherein the orientation index zone reflects at least two times the light reflected when no strip is present in the apparatus.

11. In a system for determining the presence or quantity of an analyte in a liquid applied to a test strip and inserted into an apparatus, a method for determining that the strip has been properly oriented in said apparatus, said method comprising:
   inserting said strip into said apparatus, said strip comprising a portion having liquid applied thereto, said portion having an area on a major surface of said strip defining a reaction zone, said reaction zone varying in reflectance as a function of the quantity of analyte in the applied liquid and said strip further comprising an orientation index zone positioned to lead said strip as it is inserted into said apparatus, said orientation index zone having a contrasting reflectance relative to that of the area of the major surface contiguous to the orientation index zone;
   determining the reflectance of the major surface of the strip by directing light at a fixed position in the pathway of the strip as it is inserted and detecting the reflected light;
   detecting the presence or absence of reflected light corresponding to the passage of said orientation index zone past said fixed position as the strip is inserted into said passageway.

* * * * *